United States Patent [19]

Osaki et al.

[11] Patent Number: 4,801,862

[45] Date of Patent: Jan. 31, 1989

[54] METHOD FOR MEASURING COMPLEX DIELECTRIC CONSTANT OR COMPLEX MAGNETIC CONSTANT OF MATERIALS IN THREE-DIMENSIONAL DIRECTIONS

[75] Inventors: Shigeyoshi Osaki, Takarazuka; Kiyokazu Sakai, Nishinomiya; Kimiyoshi Uranishi, Ibaragi, all of Japan

[73] Assignee: Kanzaki Paper Manufacturing Co., Ltd., Tokyo, Japan

[21] Appl. No.: 17,549

[22] Filed: Feb. 24, 1987

[30] Foreign Application Priority Data

Feb. 24, 1986 [JP] Japan .................... 61-39520

[51] Int. Cl.[4] ............................................. G01N 22/00
[52] U.S. Cl. .................................. 324/585 C; 324/585 A
[58] Field of Search ............. 324/58 R, 55.5 R, 58 A, 324/58.5 A, 58 B, 58.5 B, 58 C, 58.5 C

[56] References Cited

U.S. PATENT DOCUMENTS

| 4,087,746 | 5/1978 | Kanae | 324/58.5 B X |
| 4,211,970 | 7/1980 | Fitzky et al. | 324/58.5 A X |
| 4,257,001 | 3/1981 | Partain et al. | 324/58.5 A X |
| 4,507,602 | 3/1985 | Aquirre | 324/58.5 R X |
| 4,581,575 | 4/1986 | Osaki et al. | 324/58.5 R X |

Primary Examiner—Reinhard J. Eisenzopf
Assistant Examiner—Robert W. Mueller
Attorney, Agent, or Firm—Morgan & Finnegan

[57] ABSTRACT

Method for measuring complex dielectric or magnetic constant of materials in three-dimensional directions comprising the steps of: inserting a specimen held by a rotary holder into a slit which is provided in such a position corresponding to the antinode or belly portion of electric or magnetic field of a cavity resonator that the slit fully turns around the four-side walls of the cavity resonator in a plane perpendicular to the axis thereof to rotatably accommodate the holder about the axis; measuring the respective resonant frequencies $f_1$ and $f_2$ and the respective Q-values $Q_1$ and $Q_2$ of the cavity resonator before and after inserting said specimen into the split; and calculating the complex dielectric or magnetic constant for each of some rotation angles of the holder and each of some insertion dispositions of the specimen to the holder.

2 Claims, 4 Drawing Sheets

METHOD FOR MEASURING COMPLEX DIELECTRIC CONSTANT OR COMPLEX MAGNETIC CONSTANT OF MATERIALS IN THREE-DIMENSIONAL DIRECTIONS

TECHNICAL FIELD

The present invention relates to method for measuring complex dielectric constant or complex magnetic constant of materials using high-frequency electro-magnetic field in three-dimensional directions.

BACKGROUND ART

The dielectric constant or dielectric loss of a dielectric, and the magnetic constant or magnetic loss of a magnetic substance make up an extremely important characteristic of a variety of electrically insulated materials or magnetic materials, respectively. First, respecting the dielectric characteristics, since the dielectric loss can also be applied to high-frequency heating process, these important characteristics are critically measured in conjunction with a wide variety of materials for application to electric industries and communication technologies. Furthermore, those who are concerned in the academic field measure anisotropy of the dielectric constant of crystals.

Conventionally, either audio frequencies or high frequencies are widely made available for measurement of electrical properties of those materials mentioned above either by making up a capacitor using specimen made from metal-evaporated electrodes, or by filing up a cavity resonator with specimen materials, or by adhering specimen onto walls of the cavity resonator.

However, even those conventional materials made from either sheets or fibers not intended for electrical applications have their own anisotropy related to dielectric constant, dielectric loss, or dielectric tangent, which can usefully be made available for the index for checking to see constancy and process compatibility of those materials. For example, any variation of the quality and blended amount of pigment, filler agent, and other additives mixed into plastic material appears as the varied dielectric constant and loss. Likewise, even the slightest variation of the elongation of plastic material appears as the anisotropy of the dielectric constant and loss. Reflecting this, if either dielectric constant, dielectric loss, or dielectric tangent, or the anisotropy of these can easily be measured in the production site, these values can effectively be used for the index in following up quality control of products.

On the other hand, not only sheet-like or web-like materials, but there are a variety of functional materials widely being used, whose sections are in the shape of either rectangular, circular, or thin and lengthy like yarns. Although any conventional system can measure the dielectric constant and others of materials having two-dimensional expansion in the configuration, as mentioned above, such a conventional system cannot measure dielectric requirements of specimens like substantially thick material, linear specimen, twines, or the like. In particular, these is no practical system that allows the test operator to easily and quickly implement measurement of the dielectric requirements in factories against extremely thin materials.

Next, respecting the magnetic materials, conventionally, magnetic tapes and disks are manufactured by coating blends of ferrite fine powder and binder agent on a plastic sheet. However, since fine powder of ferrite is made from needle-like crystals, some of these crystals are likely to be oriented in specific directions when being coated onto a plastic substrate in accordance with viscosity of the binder agent itself. Although the orientation of these ferrite powders could affect the eventual performance characteristic of magnetic tapes or disks, since there was no means for actually measuring the orientation degree in factories, neither research nor control has positively been followed up over the orientation characteristic of fine powders of ferrite. Recently, to implement high-density recording of data signals on a magnetic tape or disk, a system has been introduced for applying magnetic field onto the tape surface in the vertical direction. When applying this process, desirably, needle crystals of fine powder of ferrite should vertically be oriented to the tape surface. Although this can be realized by vertically applying magnetic field onto the plastic surface before the coated layer of ferrite dries and hardens itself, actually, no means has ever been made available for easily and quickly checking and confirming the realized orientation of coated layer of ferrite materials.

DISCLOSURE OF THE INVENTION

The invention overcomes those problems mentioned above by providing novel method capable of easily and quickly measuring three-dimensional dielectric characteristics or three-dimensional magnetic constant of those specimens having an extremely thin or fine configuration.

In brief, the method for measuring the dielectric constant according to the invention comprises the steps of: inserting a specimen held by a rotary holder into a slit which is provided in such a position corresponding to the antinode, or belly portion of electric field of a cavity resonator that the slit can fully turns four-side walls of the cavity resonator in the direction perpendicular to the axis thereof to rotatably accommodate the holder about the axis; measuring the respective resonant frequencies $f_1$ and $f_2$ and the respective Q-values $Q_1$ and $Q_2$ of this cavity resonator before and after inserting the specimen into this slit; and calculating complex dielectric constant $\epsilon' - j\epsilon''$ from equations $$\epsilon' = 1 - A_1 \cdot \frac{f_2 - f_1}{f_2}$$

$$\epsilon'' = \frac{A_1}{2} \left( \frac{1}{Q_2} - \frac{1}{Q_1} \right)$$

for each of some rotation angles of the holder, and each of some insertion dispositions of the specimen to the holder when setting up constant $A_1$ in accordance with the configuration and dimension of the cavity resonator, the oscillation made, and the configuration and attitude of this specimen.

In another aspect of the invention, the method for measuring magnetic constant of materials in three-dimensional directions comprising the sequential steps of: inserting a specimen held by a rotary holder into a slit which is provided in such a position corresponding to the antinode, or belly portion of magnetic field inside of a cavity resonator that the slit can fully turn around four-side walls of the cavity resonator in the direction perpendicular to the axis thereof to rotatably accommodate the holder about the axis; measuring the respective resonant frequencies $f_1$ and $f_2$, and the respective Q values $Q_1$, and $Q_2$ of the cavity resonator before and after inserting said specimen into the slit; and calculating complex magnetic constant $\mu'$ and $\mu''$ of objective material from equations $$\mu' = 1 + A_2 \cdot \frac{f_1 - f_2}{f_2}$$

$$\mu'' = \frac{A_2}{2} \left( \frac{1}{Q_2} - \frac{1}{Q_1} \right)$$

for each of some rotation angles of the holder, and each of some insertion dispositions of the specimen to the holder, using coefficient $A_2$ which is dependent on the configuration and dimension of the cavity resonator, the oscillation mode, the configuration of the objective specimen, and the attitude of inserting said specimen into said cavity resonator.

ADVANTAGES

First, the differences between conventional systems of the dielectric constant measurement and the system according to the method of the invention are described below.

First, any conventional system either keeps the cavity resonator completely being closed or provides a pair of extremely small circular holes in the antinode, or belly portion of the cavity resonator without providing any slit at all. Conversely, the system according to the invention provides a slit which transverses the cavity resonator so that the specimen can be inserted through it. As a result, any conventional system causes much inconvenience when setting the specimen inside of the cavity resonator, and yet, it cannot rotate the specimen inside of this cavity resonator. Conversely, since the system related to the invention allows the specimen to easily be inserted into and removed from the cavity resonator, and in addition, it allows the specimen to rotate itself as required, the system can easily measure the anisotropy of the specimen in three-dimensional directions.

Second, any conventional system uses a specimen having a considerable thickness and volume enough to block the section of cavity resonator, or it uses a sheet-like specimen having a considerable size fully occupying the inner sectional area of the cavity resonator so that the inner wall surface of the cavity resonator can fully be covered, thus eventually requiring a specimen having a large area. Conversely, the system according to the invention merely needs a compact-size specimen enought to occupy part of the sectional area of the cavity resonator without requiring the specimen to fully occupy the sectional area of the cavity resonator.

When placing any dielectric material in and across the belly portion of the electric field inside of the cavity resonator, resonant frequencies vary themselves. The system according to the invention measures the dielectric constant of specimen by referring to the deviation of resonant frequencies.

Assume that the resonant frequency before inserting a specimen into the slit is $f_1$ and the resonant frequency with the specimen being inserted into the slit $f_2$, while defining the complex dielectric constant of the specimen to be $\epsilon^* = \epsilon' - j\epsilon''$, then $\epsilon'$ and $\epsilon''$ can be expressed by the equation shown below.

$$\epsilon' = 1 - A_1 \frac{f_2 - f_1}{f_2} \quad (1)$$

Figure 1A:
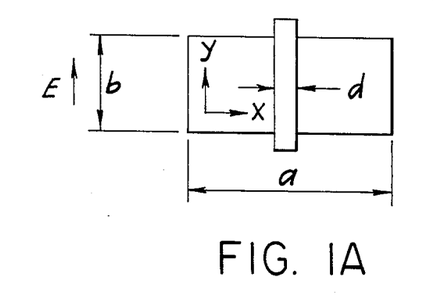
FIGS. 1A and 1B are respectively the simplified diagrams illustrating the method of setting a dielectric specimen into the cavity resonator according to the invention.
Figure 1B:
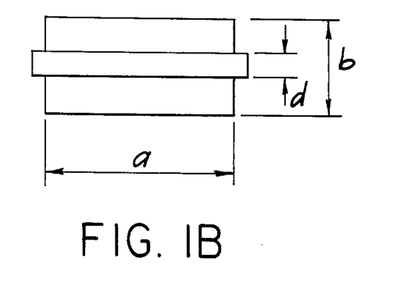

If the Q-values of the cavity resonator before and after inserting the specimen are $Q_1$ and $Q_2$, respectively, $\epsilon''$ is denoted by the equation shown below.

$$\epsilon'' = \frac{A_1}{2} \left( \frac{1}{Q_2} - \frac{1}{Q_1} \right) \quad (2)$$

where $A_1$ denotes the coefficient determined by the dimensions of the cavity resonator. Oscillation mode, and the specimen, and also by positions of these. Assume that the cavity resonator has the length c, rectangular sectional surface a×b, while a slit having gap e is provided in the center of the vertical direction (not shown). Now, assume that oscillation occurs in TE10l mode, electrical field is present in parallel with direction y and both the x and z directional components are zero, when a specimen having width d and thickness t ($d \leq a$, $d \leq b$, $t \leq e$) is inserted into the slit as shown in FIGS. 1A and 1B, taking FIG. 1A for example, coefficient $A_1$ is denoted by the equation shown below.

$$A_1 = \frac{ac}{t \sin^2 \frac{l\pi(c-e)}{2c} \left( d + \frac{a}{\pi} \sin \frac{d\pi}{\epsilon} \right)} \quad (3)$$

When dealing with FIG. 1B, the coefficient $A_1$ is given by the equation shown below.

$$A_1 = \frac{bc}{td \sin^2 \frac{l\pi(c-e)}{2c}} \quad (4)$$

These equations (3) and (4) can be made available until the area of the specimen fully occupies the section of the cavity resonator. Note that l denotes the degree number, which can used in any odd number. If the value of d is significantly less than "a", equation (3) can be replaced by equation (5) shown below.

$$A_1 = \frac{ac}{2td \sin^2 l \frac{\pi}{2} \frac{c-e}{c}} \quad (5)$$

First sin term in the equation (3) and the sin term in the equations (4) are substantially the comensatory terms caused by slit, where 1 is presented when e=0. Since the value of e is significantly less than c, taking FIG. 1A for example, coefficient A can approximately be denoted by the equation shown below.

$$A_1 = \frac{ac}{2td} \quad (6)$$

Conversely, when dealing with FIG. 1B, coefficient $A_1$ is denoted by the equation shown below.

$$A_1 = \frac{bc}{td} \quad (7)$$

Since denominator td in the above equations denoting coefficient $A_1$ is substantially the sectional area of specimen, it is possible for the system to also use any specimen such as linear specimen having circular section, filament-twisted specimen, tape-like specimen composed of a plurality of linear materials aligned in parallel with each other, or the like by inserting sectional areas of these specimens into denominator td of respective equations. Coefficient $A_1$ can be calculated by applying the following equation for determining complex dielectric constant when d=a and d=b are present as the eventual value of the width d of the specimen shown in FIG. 1A and B, i.e., when the specimen surface fully occupies the section of the cavity resonator.

$$A_1 = \frac{c - e - \frac{c}{l\pi} \sin \frac{l\pi(c-e)}{c} + 2e \sin^2 \frac{l\pi(c-e)}{2c}}{t \sin^2 \frac{l\pi(c-e)}{2c}} \quad (8)$$

Energy loss W is denoted to be $W \propto f\epsilon''E^2$ where f is frequency and E is the intensity of electric field. Since power loss is caused by effect of $\epsilon''$, the effect of $\epsilon''$ results in the lowered Q-value of the cavity resonator.

The above description refers to special cases. Generally, complex dielectric constant is calculated by the equation shown below, where E designates an electric field when no specimen is present in the position to measure them in the cavity resonator (i.e. the antinode, or belly portion of the electric field), while E' designates the electric field inside of the specimen when a specimen is inserted into the cavity resonator.

$$\frac{f_2^* - f_1^*}{f_2^*} = -\frac{(\epsilon^* - 1)\int_v \cdot 'dv}{2 \int_c | \; |^2 dv} \quad (9)$$

Note that $f^*_1$ and $f^*_2$ are respectively the complex frequencies before and after inserting specimen into the slit, while $\epsilon^*$ is the complex dielectric constant. Integration in the denominator is substantially the integration of the second power of the intensity of the electric field over the cross section of the cavity resonator. If the cavity has the rectangular section, the integration in the denominator corresponds to $acbE_O^2/2$ (where $E_O$ is the maximum amplitude of the electric field). Integration in the numerator is substantially the volume integration over the internal substance of specimen, while E.E' is the scalar product between E and E'. The value of $\epsilon^*$ can be calculated by equation 10 shown below by deforming equation 9 related to the cavity resonator having the rectangular section.

$$\epsilon^* = 1 - \frac{abcE_0^2}{2 \int_v \cdot 'dv} \cdot \frac{f_2^* - f_1^*}{f_2^*} \quad (10)$$

Taking FIG. 1A for example, independent of the sectional configuration of the specimen, $E \approx E'$ can possibly be realized. When dealing with FIG. 1B, E in the specimen is in parallel with E as denoted by the equation shown below.

$$' = \frac{2}{\epsilon + 1} \quad (11)$$

If the specimen inclines itself between the vertical and horizontal axes y and x, E' is no longer in parallel with E, thus involving complexity. Basically, when executing integration of equation 10 by introducing electric field E' in the optional rotation angle, $\epsilon^* = \epsilon' - j\epsilon''$ is solved. Since $\epsilon^*$ is substantially the complex dielectric constant in the direction of E, by rotating the specimen inside of the cavity, anisotropy of and $\epsilon^*$ and particularly $\epsilon'$, $\epsilon''$ in the direction of three axes can be made clear. The above description refers to the measurement of the dielectric constant of thin specimen transversing the cross section of the cavity resonator. The system according to the invention can determine $\epsilon$ by calculating equation 10 in conjunction with any optional shape sharing part of the section of the cavity resonator like a small circular sheet or yarns.

Now, to understand the method of measuring magnetic characteristics of the invention, the discussion is made for the inherent properties and characteristics of a waveguide unit or a cavity resonator which had been recognized as to function in vacuum. However, basically, since functions and characteristics of a waveguide unit and a cavity resonator are subjected to the velocity of electromagnetic waves, in which the velocity of magnetic waves is given by an expression $1/68 \, \mu$, if any magnetic substance is present inside of a cavity resonator, the state of magnetic oscillation inside of this cavity resonator is more easily oscillable than the state in which no magnetic substance is present.

To represent magnetic characteristic of a specimen including hysteresis, magnetic constant $\mu^*$ is hereinbelow expressed in terms of complex magnetic constant $\mu' - j\mu''$. Assume that the following conditions are provided, in which, a specimen is set to the position corresponding to the antinode, or belly portion of magnetic field inside of a cavity resonator; this cavity resonator has $f_1$ of resonant frequency and $Q_1$ of Q-value before the specimen is inserted into it and $f_2$ of the resonant frequency and $Q_2$ of Q-value after the specimen is inserted into it; and coefficient $A_2$ is provided, which is dependent on the configuration and dimension of this cavity resonator, oscillation mode, configuration, dimension, and the position (i.e., the directional relationship with magnetic field) of the objective specimen, respectively. Based on those conditions mentioned above, the following equations are established.

$$\mu' = 1 + A_2 \frac{f_1 - f_2}{f_2} \quad (12)$$

$$\mu'' = \frac{A_2}{2}\left(\frac{1}{Q_2} - \frac{1}{Q_1}\right) \quad (13)$$

Since $\mu'$ and $\mu''$ respectively denote the values of a real part and an imaginary part of the complex constant in the direction of magnetic field, when rotating the specimen against magnetic field, i.e., against the cavity resonator, actual values of $\mu'$ and $\mu''$ related to the specimen can be determined in various directions. If the specimen has such an area fully occupying the entire section of the cavity resonator, the magnitude of coefficient $A_2$ remains unaffected even when rotating the specimen. Assume that the specimen has thickness t, and the resonator is in the shape of rectangular parallelepiped and has length c in Z-axis and TE101 of the oscillation mode, then the magnetic constant is given by the equations;

$$\mu' = \frac{8f_1{}^2 C^3}{C^2 l^2 \left( t + \frac{c}{2l\pi} \sin \frac{2l\pi}{c} t \right)} \cdot \frac{f_1 - f_2}{f_2} \quad (14)$$

$$\mu'' = \frac{4f_1{}^2 C^3}{C^2 l^2 \left( t + \frac{c}{2l\pi} \sin \frac{2l\pi}{c} t \right)} \cdot \left( \frac{1}{Q_2} - \frac{1}{Q_1} \right) \quad (15)$$

Where c denotes the velocity of light, and l the number of waves inside of the cavity resonator. Actually, the cavity resonator can effectively be used when the condition l=2 is present. In conjunction with TE101 of the oscillation mode, if an even number like l=2 is applied to the device shown in FIG. 7, the antinodes, or belly portions of magnetic field are generated in both ends and the center of the cavity resonator.

Figure 7:
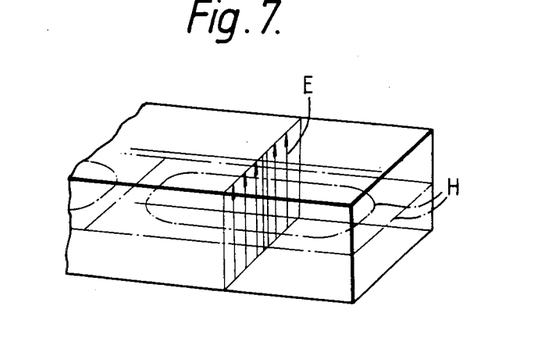
FIG. 7 is the diagram explaining TE101 of the oscillation mode generated inside of the cavity resonator.

Taking this into account, the objective specimen may be inserted into a slit provided in the center of the cavity resonator. It is also possible for the system to set the specimen to an edge surface of the cavity resonator when the number of wave is 1. In other words, the invention allows users to choose any system found more convenient for use depending on the method of oscillating the cavity resonator and the characteristic of the objective specimen.

Complex magnetic constant $\mu^*$ ($\mu^* = \mu' + i\mu''$) is calculated by the equation;

$$\frac{f_1^* - f_2^*}{f_2^*} = \frac{\int_s \{(\mu^* - \mu_0) \; ' \cdot \; - (\epsilon^* - \epsilon_0) \; ' \cdot \;\} dv}{2 \int_{vc} \epsilon_0 \; \cdot \; dv} \quad (16)$$

Where dielectric constant $\epsilon_O$ and magnetic constant $\mu_O$ are present in vacuum, while the specimen is at an optional position inside of the cavity resonator.

Where the integration in the denominator is substantially the volume integration applied to the entire inside of the cavity resonator, whereas the denumerator represents the volume integration applied to the internal substance of the specimen. E and H respectively denote the electric field and the magnetic field where no specimen is present inside of the cavity resonator. Conversely, E' and H' respectively denote the electric field and the magnetic field where the specimen is actually present inside of the cavity resonator. $\epsilon^*$ denotes complex dielectric constant. $f_1^*$ and $f_2^*$ are respectively the complex frequencies when the specimen is absent from and present in the cavity resonator. The specimen is set at the antinode, or belly portion of magnetic filed. Since no electric field is present at the belly portion of magnetic field when TE101 of the oscillation mode is activated, the second term in the integrated denumerator of the above equation is zero. Thus, the above equation 13 is rewritten into $$\frac{f_1^* - f_2^*}{f_2^*} = \frac{(\mu^* - \mu_0) \cdot \; ' \cdot \; dv}{\frac{2}{c^2} \; ' \cdot \; dv} \quad (17)$$

In conjunction with the equation 16, if the volume of the specimen is significantly less than that of the cavity resonator, the relationships E'=H and E'=H are present in space other than that is occupied by the specimen. In regard to the denominator, since the integration related to the specimen does not substantially contribute the integration of the entire cavity resonator at all, the denominator denotes electromagnetic energy present inside of the cavity resonator, which eventually becomes constant after determining the modes of the cavity resonator and oscillation. Consequently, value A2 can be determined by first executing integration of the denumerator of equation 17 in accordance with the configuration, dimension, and the direction of the specimen, followed by solution of $\mu^*$. The method according to the invention can effectively be applied to the measurement of the magnetic anisotropy of those specimens having a variety of configurations including square, rectangular or circular sections, or lengthy and narrow configuration like yarns whose length extends itself outward from the slit, or any which has a configuration smaller than the aperture of the cavity resonator for example.

BRIEF DESCRIPTION OF THE DRAWINGS

The invention will be better understood from the detailed description given hereinbelow and the accompanying drawings which are given by way of illustration only, and thus are not limitative of the invention in which.

DETAILED DESCRIPTION OF THE PREFERRED EMBODIMENTS

Figure 2:
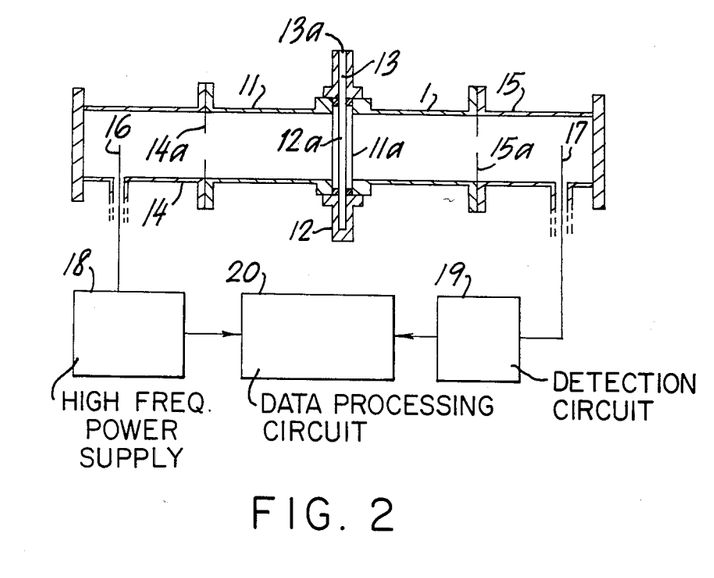
FIG. 2 is the longitudinal sectional diagram of the constitution of the preferred embodiment achieving the method of dielectric-measurement according to the invention.

FIG. 2 shows one of the preferred embodiments dielectric-measurement of the invention. Cavity resonator 11 having the rectangular cross section is cut off in the intermediate position to form a slit 11a circling over the four-side walls of the cavity resonator. In the slit 11a, a disk-shaped specimen holder 12 is inserted so that it can freely rotate itself. The specimen holder 12 is provided with a circular opening 12a spreading over the cross sectional area of the cavity 11. From the peripheral wall defining the opening 12a of the holder 12, peripheral groove 13 is provided which communicates through a segmental inlet 13a to the outer periphery of the holder 12. Specimen is inserted through the inlet 13a into this groove 13, with the opposite surfaces preferably being sandwiched by a pair of thin and transparent protection films (not shown) without any orientation characteristic. Short-length coaxial waveguide converters 14 and 15 are respectively connected to both ends of the cavity resonator 11 by putting partition walls 14a and 15a each having a small aperture in its central portions. Antenna 16 and 17 are respectively inserted into the coaxial waveguide converters 14 and 15. Antenna 16 is electrically connected to high-frequency power-supply source 18 for oscillating the cavity resonator 11, whereas antenna 17 is connected to detection circuit 19. The power supply source 18 has variable high frequencies. Voltage output from the detection circuit 19 is delivered to data-processing circuit 20 so that the maximum voltage value can be detected. High-frequency power-supply source 18 delivers the frequency-data to the data-processing circuit 20, which then reads frequencies $f_1$ and $f_2$ resulting in the maximum detection output before and after inserting the specimen into the slit. The data-processing circuit 20 then obtains data $Q_1$ and $Q_2$ from the half-power width of the resonant curve in order to calculate values $\epsilon'$ and $\epsilon''$ which are real and imaginary parts of a complex $\epsilon^*$, respectively from equations 1, 2, 6 and 7 shown in the preceding description. It also computes the degree of the orientation from calculated complex values $\epsilon_1^*$ and $\epsilon_2^*$ when the position of the specimen is oriented in two directions as shown in FIGS. 1A and B, respectively.

Experimental Result 1

Inventors measured dielectric constant and dielectric loss values by arranging the following: Using the apparatus shown in FIG. 2 and fine-width specimen made from unelongated polyethylene terephthalate having 0.2 mm of thickness, 5 mm of width, and 100 mm of length, being composed of molecules each having confirmed non-orientation characteristic; (a) a specimen made from the above material was set to allow the longitudinal axis thereof to be aligned in parallel with the direction of electric field (as shown in FIG. 1A); (b) a specimen made from the above material was set to allow the longitudinal axis thereof to be aligned perpendicular to the direction of electric field (as shown in FIG. 1B); (c) a specimen made from the above material was set to allow the direction of the thickness thereof to be aligned in parallel with the direction of electric field (substitute the thickness t for the width d shown in FIG. 1B); and (d) a specimen made from the above material was set to allow the direction of the thickness of the specimen to be aligned perpendicular to the direction of electric field (substitute the thickness t for the width d shown in FIG. 1A), respectively. Table 1 denotes the dielectric constant and the dielectric loss measured from the above tests. It clearly indicates that the dielectric constant and dielectric loss in the three-dimensional directions satisfactorily match each other and there is no orientation characteristic in molecules at all.

TABLE 1

| | Dielectric constant ($\epsilon'$) | Dielectric loss ($\epsilon'$) |
|---|---|---|
| (a) E//Longitudinal axis | 2.764 | $2.28 \times 10^{-2}$ |
| (b) E $\perp$ Longitudinal axis | 2.780 | $2.25 \times 10^{-2}$ |
| (c) E//Direction of thickness | 2.796 | $2.29 \times 10^{-2}$ |
| (d) E $\perp$ Direction of thickness | 2.791 | $2.25 \times 10^{-2}$ |

Experimental Result 2

Inventors measured dielectric constant and dielectric loss of specimens by applying the procedures identical to those which were made available for the first experiment except for the application of fine-width specimens made from polyethylene terephthalate uni-axially elongated in the longitudinal axis direction, and as a result, dielectric constant $\epsilon'$ and dielectric loss $\epsilon''$ shown in Table 2 were produced. As shown in Table 2, since the dielectric constant in the longitudinal axis direction corresponding to uni-axially elongated direction increases and conversely dielectric loss decreases. In contrast the non-orientation characteristic of molecules of the first experiment, it is clear from this second experiment that molecules could be provided with a specific orientation characteristic by applying uni-axial elongation process.

TABLE 2

| | Dielectric constant ($\epsilon'$) | Dielectric loss ($\epsilon'$) |
|---|---|---|
| (a) E//Longitudinal axis | 2.902 | $1.60 \times 10^{-2}$ |
| (b) E $\perp$ Longitudinal axis | 2.675 | $2.20 \times 10^{-2}$ |
| (c) E//Direction of thickness | 2.890 | $2.80 \times 10^{-2}$ |
| (d) E $\perp$ Direction of thickness | 2.710 | $3.20 \times 10^{-2}$ |

If the length of the specimen is too short and cannot directly be inserted into the holder, the system according to the invention allows the specimen to be either adhered to or sandwiched between sheets having no orientation characteristic before inserting these sheets into the holder.

Figure 10:
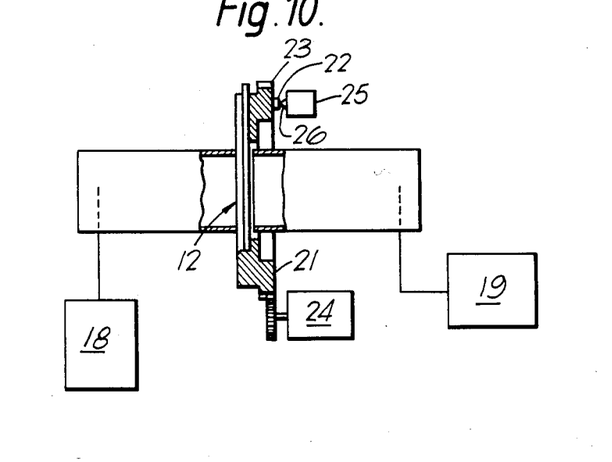
FIG. 10 is the longitudinal sectional view and circuit diagrams showing one of various modifications applicable to the three-dimensional dielectric-constant measuring apparatus shown in FIG. 2.

In the FIG. 10, there is shown the preferred arrangement of the rotary holder and a driving mechanism associated thereto.

The holder 12 as shown in FIG. 10 has a peripheral ridge 21 which is provided with at least one positioning pin 22 on the end surface thereof. On the outer circumferential surface of the peripheral ridge 21, gear teeth 23 is formed, which engages a gear member secured to the driving shaft of a motor 24 to rotate the holder 12 with a specimen to a desired, or generally about the right angle. The motor 24, of course, secured relative to the holder 12. Facing the end surface of the peripheral ridge 21, a limit switch 25 is secured relative to the cavity resonator, which has an actuator 26 to be depressed by the positioning pin 22 of the holder 12. Thus, the limit switch 25, upon the actuator 26 being depressed, changes its state to inform a motor driving circuit (not shown) with the zero-angular position of the holder 12.

Figure 11:
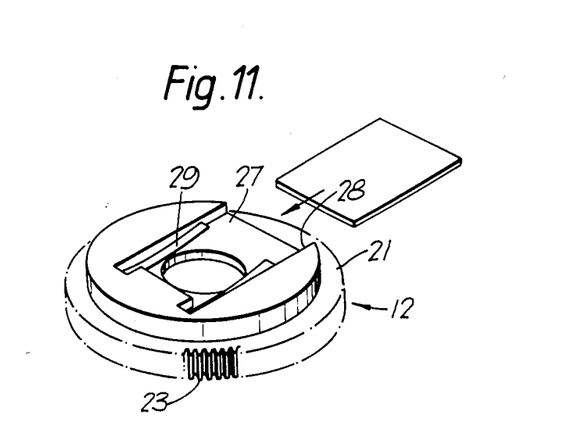
FIG. 11 is the perspective view of the specimen holder applicable with the above modification.

In FIG. 11, there is shown the other surface of the holder 12 on which an engraved rectangle 27 to accommodate a specimen is provided. One of the four sides of the rectangle 27 makes an inlet 28 insert a specimen therethrough into the engraved rectangle. Each of two-side walls starting with the opposite ends of the inlet 28 of the engraved rectangle 27 is provided with a leaf spring 29 to hold the associated side of specimen to be settled.

The above constitution as shown in FIGS. 10 and 11 is applicable to measuring the magnetic characteristics of the invention by modifying dimentional proportion, and the material thereof, properly.

Figure 4:
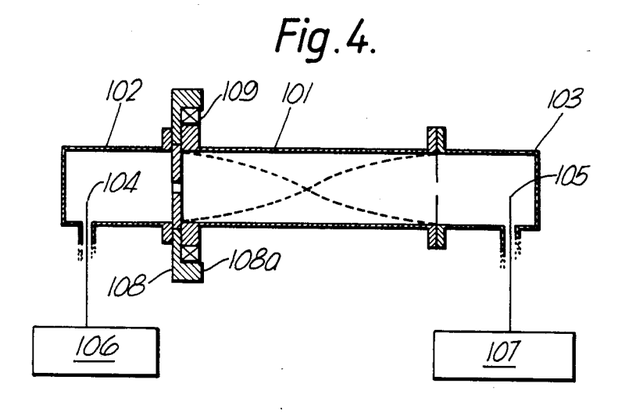
FIG. 4 is the longitudinal sectional diagram of the preferred embodiment executing the method of magnetic-measurement according to the invention.

FIG. 4 shows the simplified schematic diagram of the apparatus embodied in accordance with the method for magnetic measurement of the invention.

Both ends of cavity resonator 101 having a rectangular cross section are connected to coaxial waveguide converter 102. Antenna 104 is inserted into coaxial waveguide converter 102 for transmitting waves oscillating cavity resonator 101. Receiving antenna 105 is inserted into coaxial waveguide converter 103. Transmitting antenna 104 is connected to oscillator 106 via a coaxial cable, whereas the receiving antenna 105 is connected to detection circuit 107 via a coaxial cable. A partition wall having a small aperture at the central portion thereof is provided between cavity resonator 101 and coaxial waveguide converter 103, thus making up the edge wall of cavity resonator 101. Disk-shaped specimen-holder 108 is inserted into slit between cavity resonator 101 and coaxial waveguide converter 102 so that it can freely turn itself. At the same time, this disk-like specimen holder 108 makes up the partition wall between cavity resonator 101 and coaxial waveguide converter 102. A small aperture is provided at the central portion of the specimen-holder 108 so that electrical oscillation inside of coaxial waveguide converter 102 can leak into cavity resonator 101 through this hold before driving cavity resonator 101.

Figures 5, 6:
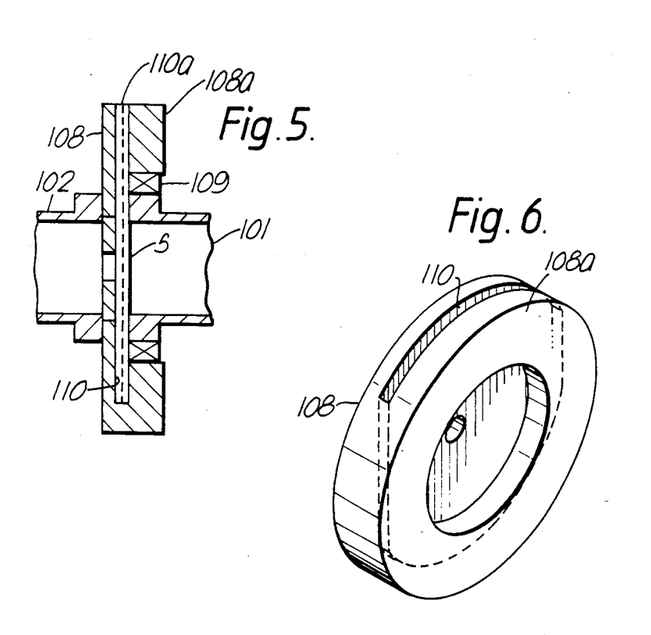
FIG. 5 is the partially enlarged sectional diagram of the FIG. 4.
FIG. 6 is the perspective view of the disk-like specimen holder constituted in accordance with the invention.

FIG. 5 shows the detail of the specimen-holder 108 and the associated parts in its cross section. Convex 108a is provided on the peripheral portion of holder 108, while the inner circumference of this convex 108a is held by bearing 109 coupled to a flange at an edge of cavity resonator 101, thus allowing holder 108 to freely rotate itself. Gear surface is formed (not shown) to the outer circumference of convex 108a and connected to drive motor (not shown). Holder 108 is provided with gap 110 between the convex 108a and the one disk surface at the same side in parallel with an inlet slit 110a communicated to the gap present in part of the outer circumference of holder 108. Specimen S is inserted through the inlet 110a into gap 110 in a condition being sandwiched by a pair of protection films (not shown) made from magnetically non-oriented sheets. In this preferred embodiment, oscillation mode is underway at $l=1$ in $TE_{10}l$, while the both ends of cavity resonator 101 generate the antinodes, or belly portion of the oscillation of magnetic field as shown in FIG. 4.

As mentioned earlier, since the effect of $\mu$ of the specimen is generated as deviation of resonant frequencies of the cavity resonator, any deviation of the resonant frequencies can visually be observed as lowered output from detector 107 by fixing the needed frequency at the resonant frequency when no specimen is present in the cavity resonator. If such a specimen having an area fully occupying the section of the cavity resonator were used, due to the rotation of the specimen, the magnitude of coefficient $A_2$ which is substantially the factor of the configuration and position of specimen remains unchanged, and as a result, elliptical records can be obtained by recording the relationship between the angle of the rotation of holder 108 and the detect output by applying polar coordinate while rotating the specimen. Consequently, anisotropy of $\mu$ like the orientation degree of ferrite particles for example can be found by the ratio between the long and short diameters of the elliptical records. If a specimen having an extremely narrow width to cause its length to extend outward from the slit is used, coefficient $A_2$ is variable by the angle of the rotation of the specimen, and thus, since anisotropy of $\mu$ cannot immediately be detected from the recorded relationship between the wave-detect output and the rotation angle of the specimen, calculations using equation 14 are required. When measuring magnetic constant of any specimen which is smaller than the aperture of a waveguide unit or a specimen taken out of a magnetic tape, if the configuration of a specimen cut out into a disklet, then factor $A_2$ related to the configuration and position of the specimen remains unchanged in spite of the rotation of the holder with the specimen, even when the prepared specimen is simply placed in the center of holder 108, or when the specimen is bonded against a non-oriented sheet with non-oriented adhesive agent, or when the specimen is sandwiched between a pair of non-oriented sheets. Accordingly, anisotropy of the specimen in three-dimensional directions can immediately be detected by recording the relationship between the wave-detection output and the angle of the rotation of the specimen using polar coordinate.

Figure 8:
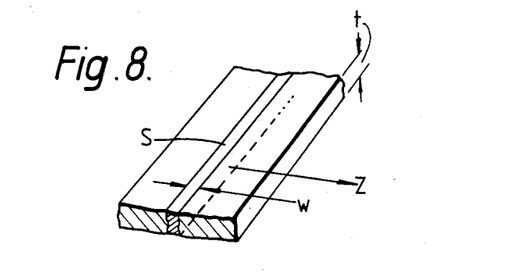
FIG. 8 is the diagram explaining the method of cutting off a magnetic specimen from the original substrate for measuring anisotropy of the specimen in the direction of thickness.

For example, when dealing with a magnetic tape or disk with ferrite particles being oriented in the direction of thickness, as shown in FIG. 8, specimen S is thinly cut off from either a magnetic tape or a magnetic disk, and then, the specimen is inserted into the cavity resonator so that direction Z in parallel with the surface of the tape or disk can be aligned in the axial direction of the cavity resonator. Assume that the specimen has thickness w against width t, the cavity resonator has length c and the section a x b, while the specimen is set in position as shown by X and Y of FIG. 9, in which a specific vibration mode TEL (where $l=1$) is introduced.

The denominator of the preceding equation 17 is expressed by $$\frac{1}{2C^2} abcE_0^2 \qquad (18)$$

Figure 9:
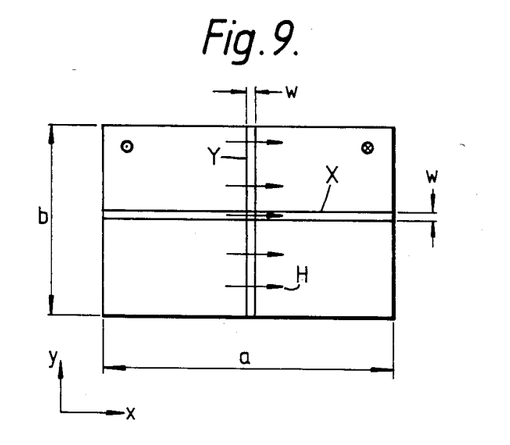
FIG. 9 is the diagram explaining the state in which the cut-off magnetic specimen is inserted into the cavity resonator.

When the specimen is placed in position as shown by Y of FIG. 9, since magnetic flux has equivalent density in the front and rear portions of the specimen in the direction of the lime of magnetic force in the field H, magnetic field inside of the specimen remains in the state of $H/\mu$. Since magnetic field H is constant in the direction y, the denumerator of the preceding equation 17 is expressed by $$\frac{\mu - 1}{\mu} \omega tbH_0^2 \qquad (19)$$

where $H_O$ denotes the maximum intensity of magnetic field. Based on expressions 18 and 19, the following equation is established.

$$\frac{f_1 - f_2}{f_2} = \frac{\dfrac{\mu - 1}{\mu} \omega tbH_0^2}{\dfrac{1}{2C^2} abcE_0^2} \qquad (20)$$

Value μ can be calculated from the above equation by applying the following equation.

$$\mu = \frac{1}{1 - \frac{1}{\omega t b} \frac{abcE_0^2}{2C^2H_0^2} \frac{f_1 - f_2}{f_2}} \quad (21)$$

When the specimen is set in position as shown by X of FIG. 9, if the section of the specimen is significantly small, then independent of the presence or absence of the specimen, magnetic field ambient the specimen remains constant. Likewise, independent of the presence or absence of the specimen, magnetomotive force of the magnetic force line circling over the cavity resonator by permeating through the specimen in the direction X also remains constant. This condition is denoted by H′=H. Variation of the intensity of magnetic field in the direction of x is denoted by the equation shown below.

$$H = H_0 \sin \frac{\pi x}{a} \quad (22)$$

Based thereon, the denumerator of equation 17 can be processed by expression shown below.

$$(\mu - 1)\omega t a H_0^2 / 2 \quad (23)$$

This provides the equation shown below.

$$\mu = 1 + \frac{abc}{C^2 \omega t a} \frac{E_0^2}{H_0^2} \frac{f_1 - f_2}{f_2} \quad (24)$$

Note that equation 21 represents the magnetic constant in the direction of the thickness of a magnetic tape or disk, whereas equation 24 represents value in the direction in parallel with the surface of a magnetic tape or disk.

INDUSTRIAL APPLICABILITY

Figure 3:
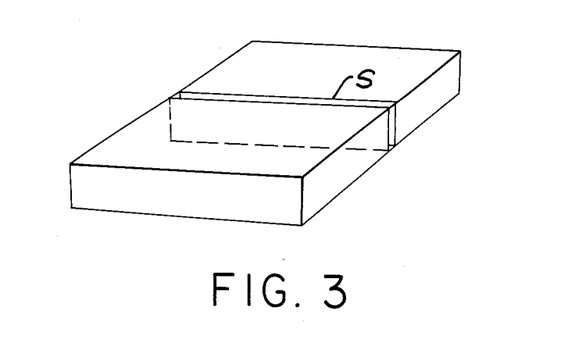
FIG. 3 is the simplified diagram illustrating the method of cutting out a specimen for measuring dielectric constant in the direction of thickness.

In principle, the method according to the invention does not substantially limit the applicable shape of the specimen, but it effectively allows the system to measure the dielectric requirements of specimens fully occupying the entire cross section or merely occupying part of the cross sectional area of the cavity resonator. Furthermore, of course, the method for three-dimensional measurement allows calculation of the dielectric constant of the objective specimen in the direction of its thickness by cutting it off from a sheet specimen as shown in FIG. 3 and setting it to the predetermined position as shown in FIG. 1B, and in addition, two-directional dielectric constant in parallel with the sheet surface can also be calculated. This allows the method according to the invention to securely and correctly measure three-dimensional anisotropy of sheet materials as well. In addition, the method according to the invention easily measures the dielectric constant and anisotropy of wide variety of specimens due to the easiness of replacement and rotation of specimens, thus making it possible for the system to easily compute dielectric constant and refractive index in place of measuring refractive index and birefringence of translucent materials thus far impracticable. Some of plastic materials have an ideal relationship begween crystallization rate and the dielectric loss. Since the method according to the invention can easily make calculation of complex dielectric constant, it is possible for the factory staff to properly control the crystallization rate of plastic materials, thus effectively providing quite reliable means for properly controlling quality of materials during production processes.

While according to the second aspect of the invention, magnetic anisotropy of an objective specimen in three-dimensional directions can easily be detected by measuring variations of resonant frequencies or Q-value (variation of these can be detected as the varied output of wave-detection signals by stabilizing oscillation frequencies) by allowing the cavity resonator containing the specimen to rotate both the cavity resonator and the specimen together in the relative manner. The method according to the second aspect of the invention effectively deals with a variety of specimens including the one having a size wider than the section of the cavity resonator, or the one having a size narrower than the section of the cavity resonator, or the one made from an extremely thin material causing its length to extend outward from the section of the cavity resonator, etc.

As a result, such method of magnetic measurement allow to easily and quickly measure magnetic anisotropy of a variety of specimens in three-dimensional directions (see explanations related to FIG. 8), thus effectively and significantly promoting satisfactory quality control of a variety of complete products containing magnetic substance.

We claim:

1. Method for measuring complex dielectric constant of materials in three-dimensional directions comprising the steps of;
    inserting a specimen held by a rotary holder into a slit which is provided in such a position corresponding to the antinode or belly portion of electric field of a cavity resonator that the slit fully turns around the four-side walls of the cavity resonator in a plane perpendicular to the axis thereof to rotatably accommodate the holder about the axis;
    measuring the respective resonant frequencies $f_1$ and $f_2$ and the respective Q-values $Q_1$ and $Q_2$ of the cavity resonator before and after inserting said specimen into the slit; and
    calculating complex dielectric constant $\epsilon' - j\epsilon''$ from equations $$\epsilon' = 1 - A_1 \cdot \frac{f_2 - f_1}{f_2}$$

$$\epsilon'' = \frac{A_1}{2} \left( \frac{1}{Q_2} - \frac{1}{Q_1} \right)$$

for each of some rotation angles of the holder and each of some insertion dispositions of the specimen to the holder when setting up constant $A_1$ in accordance with the configuration and dimension of the cavity resonator, the oscillation mode, and the configuration and position of the specimen to the cavity resonator.

2. Method for measuring complex magnetic constant of materials in three-dimensional directions comprising the sequential steps of;
    inserting specimen held by a rotary holder into a slit which is provided in such a position corresponding to the antinode, or belly portion of magnetic field inside of a cavity resonator that the slit fully turns around the four-side walls of the cavity resonator in a plane perpendicular to the axis thereof to rotatably accommodate the holder about the axis;

measuring the respective resonant frequencies $f_1$ and $f_2$, and the respective Q-values $Q_1$ and $Q_2$ of the cavity resonator before and after inserting said specimen into the slit; and calculating complex magnetic constant, $\epsilon'$ and $\epsilon''$ of objective material from equations $$\mu' = 1 + A_2 \cdot \frac{f_1 - f_2}{f_2}$$

$$\mu'' = \frac{A_2}{2}\left(\frac{1}{Q_2} - \frac{1}{Q_1}\right)$$

for each of some rotation angles of the holder, and each of some insertion dispositions of the specimen to the holder, using coefficient $A_2$ which is dependent on the configuration and dimension of the cavity resonator, the oscillation mode, the configuration of the ojective specimen, and the position of inserting said specimen into said cavity resonator.

* * * * *